(12) United States Patent
Hansen

(10) Patent No.: US 9,913,634 B2
(45) Date of Patent: Mar. 13, 2018

(54) LOCKING ELEMENT FOR VASCULAR CLOSURE DEVICE

(75) Inventor: James G. Hansen, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1891 days.

(21) Appl. No.: 12/389,847

(22) Filed: Feb. 20, 2009

(65) Prior Publication Data

US 2010/0217308 A1 Aug. 26, 2010

(51) Int. Cl.
- *A61B 17/00* (2006.01)
- *A61B 17/03* (2006.01)
- *A61B 17/04* (2006.01)

(52) U.S. Cl.
CPC .......... *A61B 17/0057* (2013.01); *A61B 2017/00654* (2013.01); *A61B 2017/00659* (2013.01); *A61B 2017/0474* (2013.01); *A61B 2017/0475* (2013.01); *A61B 2017/0496* (2013.01)

(58) Field of Classification Search
CPC ...... A61B 17/0057; A61B 2017/00637; A61B 2017/00641; A61B 2017/00654; A61B 2017/00601; A61B 2017/00004; A61B 2017/00606; A61B 2017/00628; A61B 2017/0417; A61B 2017/0419; A61B 2017/0477; A61B 2017/0475; A61F 2210/0004; B65H 69/04; A01K 91/04
USPC .................................... 606/213; 289/1.2, 1.5
See application file for complete search history.

(56) References Cited

U.S. PATENT DOCUMENTS

| | | | |
|---|---|---|---|
| 3,738,692 A * | 6/1973 | Martuch et al. | 289/1.2 |
| 5,021,059 A | 6/1991 | Kensey et al. | |
| 5,108,421 A | 4/1992 | Fowler | |
| 5,129,882 A | 7/1992 | Weldon et al. | |
| 5,192,300 A | 3/1993 | Fowler | |
| 5,192,302 A | 3/1993 | Kensey et al. | |
| 5,221,259 A | 6/1993 | Weldon et al. | |
| 5,222,974 A | 6/1993 | Kensey et al. | |
| 5,254,105 A | 10/1993 | Haaga | |
| 5,275,616 A | 1/1994 | Fowler | |
| 5,282,827 A | 2/1994 | Kensey et al. | |
| 5,290,310 A | 3/1994 | Makower et al. | |
| 5,292,332 A | 3/1994 | Lee | |

(Continued)

FOREIGN PATENT DOCUMENTS

| | | |
|---|---|---|
| EP | 1568326 A1 | 8/2005 |
| EP | 1671591 A1 | 6/2006 |

(Continued)

*Primary Examiner* — Christopher L Templeton
(74) *Attorney, Agent, or Firm* — Seager, Tufte & Wickhem, LLP

(57) ABSTRACT

In one illustrative example, a device for sealing an opening in a vessel wall and/or tissue tract may include an anchor, a filament, a plug, and a knot. The anchor may be configured to be disposed adjacent to an interior surface of the vessel wall adjacent the opening in the vessel wall. The filament may have a distal end coupled to the anchor and may be configured to extend proximally through the vessel opening and/or tissue tract. The plug may be disposed about at least a portion of the filament member. The knot may be disposed about the filament proximal of the plug and may be configured to move over the filament and secure the plug relative to the anchor. The knot may be independent of the filament member.

10 Claims, 4 Drawing Sheets

(56) References Cited

U.S. PATENT DOCUMENTS

| | | |
|---|---|---|
| 5,310,407 A | 5/1994 | Casale |
| 5,312,435 A | 5/1994 | Nash et al. |
| 5,320,639 A | 6/1994 | Rudnick |
| 5,342,393 A | 8/1994 | Stack |
| 5,350,399 A | 9/1994 | Erlebacher et al. |
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen |
| 5,441,517 A | 8/1995 | Kensey et al. |
| 5,443,481 A | 8/1995 | Lee |
| 5,447,502 A | 9/1995 | Haaga |
| 5,454,833 A | 10/1995 | Boussignac et al. |
| 5,478,326 A | 12/1995 | Shiu |
| 5,478,352 A | 12/1995 | Fowler |
| 5,486,195 A | 1/1996 | Myers et al. |
| 5,529,577 A | 6/1996 | Hammerslag |
| 5,531,759 A | 7/1996 | Kensey et al. |
| 5,540,715 A | 7/1996 | Katsaros et al. |
| 5,545,178 A | 8/1996 | Kensey et al. |
| 5,549,633 A | 8/1996 | Evans et al. |
| 5,571,181 A | 11/1996 | Li |
| 5,573,518 A | 11/1996 | Haaga |
| 5,591,204 A | 1/1997 | Janzen et al. |
| 5,593,422 A | 1/1997 | Muijs Van de Moer et al. |
| 5,601,602 A | 2/1997 | Fowler |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,662,681 A | 9/1997 | Nash et al. |
| 5,676,689 A | 10/1997 | Kensey et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,122 A | 3/1998 | Leschinsky et al. |
| 5,728,133 A | 3/1998 | Kontos |
| 5,728,134 A | 3/1998 | Barak |
| 5,741,223 A | 4/1998 | Janzen et al. |
| 5,782,860 A | 7/1998 | Epstein et al. |
| 5,810,884 A | 9/1998 | Kim |
| 5,830,130 A | 11/1998 | Janzen et al. |
| 5,843,124 A | 12/1998 | Hammerslag |
| 5,853,421 A | 12/1998 | Leschinsky et al. |
| 5,861,004 A | 1/1999 | Kensey et al. |
| 5,871,474 A | 2/1999 | Hermann et al. |
| 5,871,501 A | 2/1999 | Leschinsky et al. |
| 5,906,631 A | 5/1999 | Imran |
| 5,916,236 A | 6/1999 | Muijs Van de Moer et al. |
| 5,922,009 A | 7/1999 | Epstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,951,583 A | 9/1999 | Jensen et al. |
| 5,957,952 A | 9/1999 | Gershony et al. |
| 6,007,561 A | 12/1999 | Bourque et al. |
| 6,017,359 A | 1/2000 | Gershony et al. |
| 6,045,569 A | 4/2000 | Kensey et al. |
| 6,045,570 A | 4/2000 | Epstein et al. |
| 6,048,357 A | 4/2000 | Kontos |
| 6,048,358 A | 4/2000 | Barak |
| 6,054,569 A | 4/2000 | Bennett et al. |
| 6,056,768 A | 5/2000 | Cates et al. |
| 6,056,769 A | 5/2000 | Epstein et al. |
| 6,056,770 A | 5/2000 | Epstein et al. |
| 6,080,183 A | 6/2000 | Tsugita et al. |
| 6,110,184 A | 8/2000 | Weadock |
| 6,120,524 A | 9/2000 | Taheri |
| 6,126,675 A | 10/2000 | Shchervinsky et al. |
| 6,162,240 A | 12/2000 | Cates et al. |
| 6,179,863 B1 | 1/2001 | Kensey et al. |
| 6,183,496 B1 | 2/2001 | Urbanski |
| 6,190,400 B1 | 2/2001 | Van De Moer et al. |
| 6,261,309 B1 | 7/2001 | Urbanski |
| 6,296,632 B1 | 10/2001 | Luscher et al. |
| 6,296,657 B1 | 10/2001 | Brucker |
| 6,296,658 B1 | 10/2001 | Gershony et al. |
| 6,325,789 B1 | 12/2001 | Janzen et al. |
| 6,350,274 B1 | 2/2002 | Li |
| 6,368,300 B1 | 4/2002 | Fallon et al. |
| 6,368,341 B1 | 4/2002 | Abrahamson |
| 6,425,911 B1 | 7/2002 | Akerfeldt et al. |
| 6,461,346 B1 | 10/2002 | Buelna |
| 6,464,712 B1 | 10/2002 | Epstein et al. |
| 6,468,293 B2 | 10/2002 | Bonutti et al. |
| 6,475,177 B1 | 11/2002 | Suzuki |
| 6,475,230 B1 | 11/2002 | Bonutti et al. |
| 6,500,152 B1 | 12/2002 | Illi |
| 6,508,828 B1 | 1/2003 | Akerfeldt et al. |
| 6,524,328 B2 | 2/2003 | Levinson |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,569,187 B1 | 5/2003 | Bonutti et al. |
| 6,572,635 B1 | 6/2003 | Bonutti |
| 6,592,608 B2 | 7/2003 | Fisher et al. |
| 6,596,012 B2 | 7/2003 | Akerfeldt et al. |
| 6,596,014 B2 | 7/2003 | Levinson et al. |
| 6,613,070 B2 | 9/2003 | Redmond et al. |
| 6,623,509 B2 | 9/2003 | Ginn |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,682,489 B2 | 1/2004 | Tenerz et al. |
| 6,685,727 B2 | 2/2004 | Fisher et al. |
| 6,699,261 B1 | 3/2004 | Cates et al. |
| 6,712,837 B2 | 3/2004 | Åkerfeldt et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,764,500 B1 | 7/2004 | Muijs Van De Moer et al. |
| 6,780,197 B2 | 8/2004 | Roe et al. |
| 6,790,220 B2 | 9/2004 | Morris et al. |
| 6,818,008 B1 | 11/2004 | Cates et al. |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,896,692 B2 | 5/2005 | Ginn et al. |
| 6,929,655 B2 | 8/2005 | Egnelov et al. |
| 6,939,363 B2 | 9/2005 | Åkerfeldt |
| 6,942,684 B2 | 9/2005 | Bonutti |
| 6,955,683 B2 | 10/2005 | Bonutti |
| 6,964,658 B2 | 11/2005 | Ashby et al. |
| 6,969,397 B2 | 11/2005 | Ginn |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,776 B1 | 4/2006 | Houser et al. |
| 7,037,323 B2 | 5/2006 | Sing et al. |
| 7,044,916 B2 | 5/2006 | Tenerz et al. |
| 7,083,635 B2 | 8/2006 | Ginn |
| 7,192,436 B2 | 3/2007 | Sing et al. |
| 7,267,679 B2 | 9/2007 | McGuckin, Jr. et al. |
| 7,316,704 B2 | 1/2008 | Bagaoisan et al. |
| 7,322,976 B2 | 1/2008 | Yassinzadeh |
| 7,331,979 B2 | 2/2008 | Khosravi et al. |
| 7,331,981 B2 | 2/2008 | Cates et al. |
| 7,335,220 B2 | 2/2008 | Khosravi et al. |
| 2002/0002889 A1 | 1/2002 | Ashby et al. |
| 2002/0016612 A1 | 2/2002 | Ashby et al. |
| 2002/0198562 A1 | 12/2002 | Akerfeldt et al. |

(56) References Cited

U.S. PATENT DOCUMENTS

| | | |
|---|---|---|
| 2003/0088271 A1 | 5/2003 | Cragg et al. |
| 2004/0093025 A1 | 5/2004 | Egnelov |
| 2004/0098044 A1 | 5/2004 | Van de Moer et al. |
| 2004/0098046 A1 | 5/2004 | Tenerz et al. |
| 2004/0133236 A1* | 7/2004 | Chanduszko ................. 606/213 |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0049637 A1 | 3/2005 | Morris et al. |
| 2005/0085852 A1 | 4/2005 | Ditter |
| 2005/0085855 A1 | 4/2005 | Forsberg |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0267521 A1 | 12/2005 | Forsberg |
| 2005/0267528 A1 | 12/2005 | Ginn et al. |
| 2006/0004408 A1 | 1/2006 | Morris et al. |
| 2006/0030886 A1 | 2/2006 | Clark |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0100664 A1 | 5/2006 | Pai et al. |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0206146 A1 | 9/2006 | Tenerz |
| 2006/0229672 A1 | 10/2006 | Forsberg |
| 2006/0229673 A1 | 10/2006 | Forsberg |
| 2006/0229674 A1 | 10/2006 | Forsberg |
| 2006/0259074 A1* | 11/2006 | Kelleher et al. .............. 606/213 |
| 2006/0265006 A1 | 11/2006 | White et al. |
| 2006/0265007 A1 | 11/2006 | White et al. |
| 2006/0265008 A1 | 11/2006 | Maruyama et al. |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0118176 A1* | 5/2007 | Opolski et al. ............... 606/213 |
| 2007/0135842 A1 | 6/2007 | Van de Moer et al. |
| 2007/0276433 A1 | 11/2007 | Huss |
| 2008/0065121 A1 | 3/2008 | Kawaura et al. |
| 2008/0071311 A1 | 3/2008 | White et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2009/0024106 A1 | 1/2009 | Morris |
| 2010/0194110 A1* | 8/2010 | Ng ................................ 289/1.5 |

FOREIGN PATENT DOCUMENTS

| | | |
|---|---|---|
| EP | 1949859 A1 | 7/2008 |
| WO | 8911301 A1 | 11/1989 |
| WO | 2005117715 A2 | 12/2005 |
| WO | 2006078578 A2 | 7/2006 |
| WO | 2006124238 A2 | 11/2006 |
| WO | 2010096483 A1 | 8/2010 |

* cited by examiner

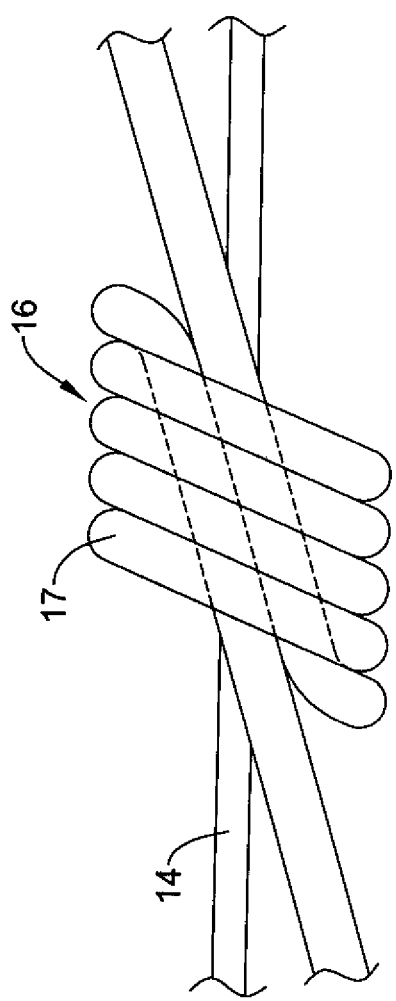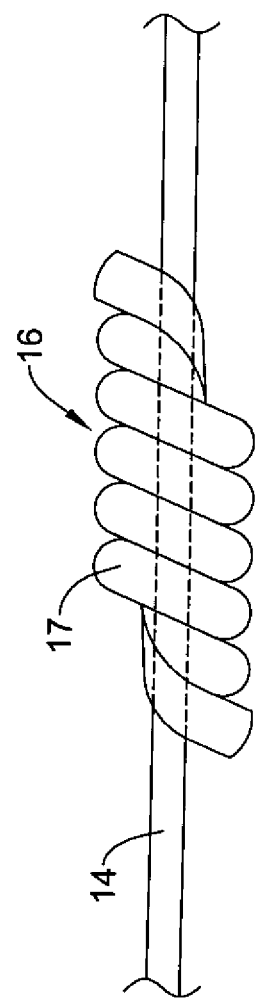

us 9,913,634 B2

LOCKING ELEMENT FOR VASCULAR CLOSURE DEVICE

FIELD

The present disclosure relates generally to medical devices and more particularly to methods and devices for closing and/or sealing punctures in tissue.

BACKGROUND

In many medical procedures, such as, for example, balloon angioplasty and the like, an opening can be created in a blood vessel or arteriotomy to allow for the insertion of various medical devices which can be navigated through the blood vessel to the site to be treated. For example, a guidewire may first be inserted through the tissue tract created between the skin, or the epidermis, of the patient down through the subcutaneous tissue and into the opening formed in the blood vessel. The guidewire is then navigated through the blood vessel to the site of the occlusion or other treatment site. Once the guidewire is in place, an introducer sheath can be slid over the guide wire to form a wider, more easily accessible, tract between the epidermis and the opening into the blood vessel. The appropriate medical device can then be introduced over the guidewire through the introducer sheath and then up the blood vessel to the site of the occlusion or other treatment site.

Once the procedure is completed, the medical devices or other equipment introduced into the vessel can be retracted through the blood vessel, out the opening in the blood vessel wall, and out through the tissue tract to be removed from the body. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. However, there is an ongoing need to provide new and improved device structures, assemblies, and/or methods for closing and/or sealing the opening in the blood vessel and/or tissue tract.

BRIEF SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

The present disclosure relates generally to medical devices and more particularly to methods and devices for closing and/or sealing punctures in tissue. In one illustrative embodiment, a device for sealing an opening in a vessel wall and/or tissue tract may include an anchor, a filament, a plug, and a knot. The anchor may be configured to be disposed adjacent to an interior surface of the vessel wall adjacent the opening in the vessel wall. The filament may have a distal end coupled to the anchor and may be configured to extend proximally through the vessel opening and/or tissue tract. The plug may be disposed about at least a portion of the filament member. The knot may be disposed about the filament proximal of the plug and may be configured to move over the filament and secure the plug relative to the anchor. The knot may be independent of the filament member.

In some cases, the knot may include a suture member having a first end, a second end, and an intermediate portion having a number of turns defining a lumen, wherein the first end and second end are passed through the lumen. In some cases, the knot may be configured to exert a compressive force on the filament.

BRIEF DESCRIPTION OF THE DRAWINGS

The invention may be more completely understood in consideration of the following detailed description of various embodiments of the invention in connection with the accompanying drawings, in which:

FIG. 2 is a schematic diagram of the illustrative knot of FIG. 1 loosely disposed about the filament shown in FIG. 1;

FIG. 3 is a schematic diagram of the illustrative knot of FIG. 1 tightly disposed about the filament shown in FIG. 1.

Figure 1:
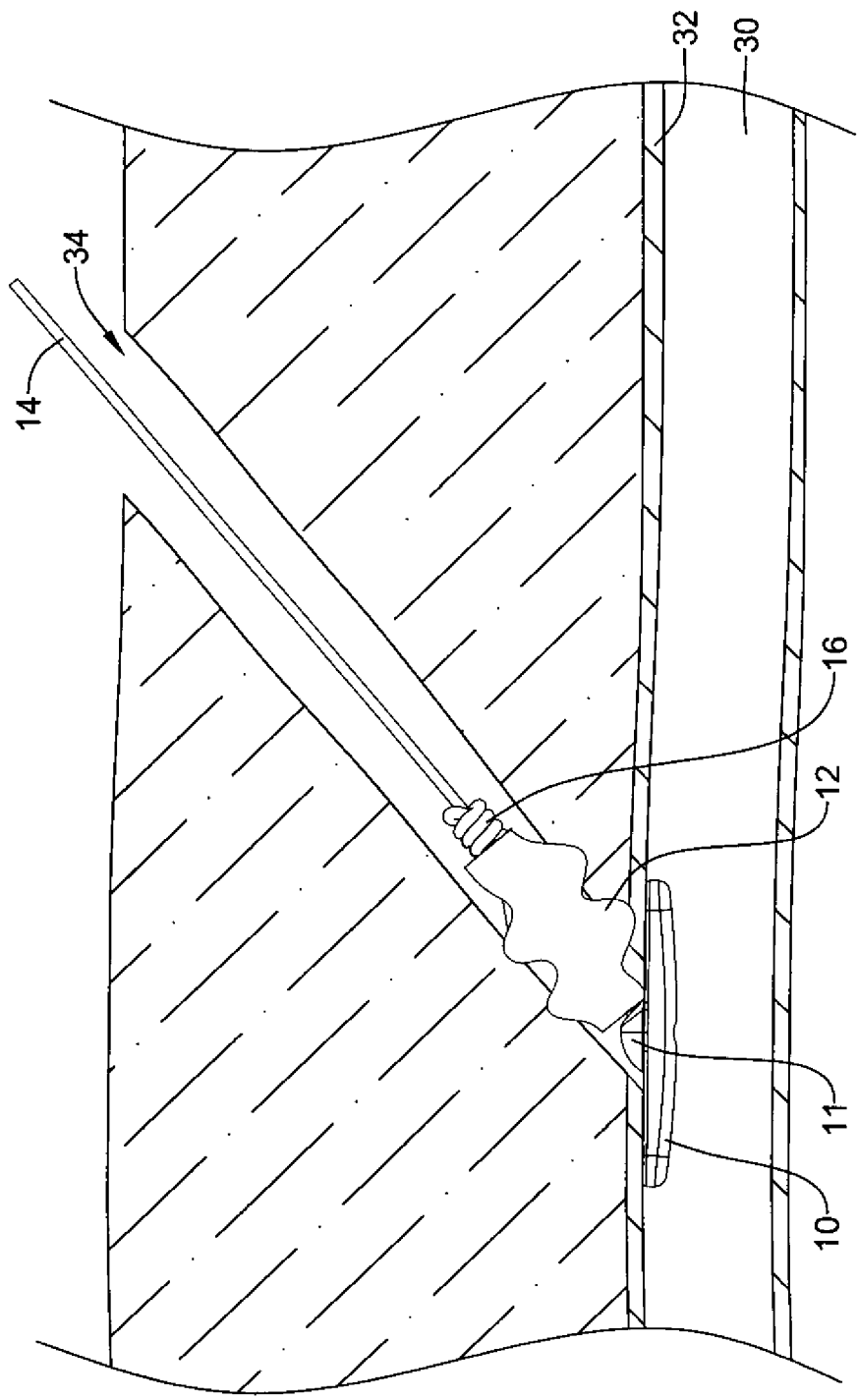
FIG. 1 is a schematic diagram of an illustrative embodiment of an anchor, a plug, a filament, and a locking element for closing and/or sealing an opening in a blood vessel and/or adjacent tissue tract.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a schematic diagram of an illustrative embodiment of an anchor 10, a plug 12, a filament 14, and a locking element 16 for closing and/or sealing an opening in a blood vessel 30 and/or adjacent tissue tract 34 that was created to gain access to the vessel to perform a medical procedure. In the illustrative embodiment, the anchor 10 may be configured to engage an interior surface of the vessel wall 32. In some cases, the anchor 10 may be configured to partially or completely occlude the opening in the vessel wall 32, as desired. The anchor 10 may include a biodegradable material so that, over time, the anchor 10 is degraded, eroded, and/or absorbed in the body. In some cases, the anchor 10 may include a PLGA, PLLA, PGA or other degradable or erodable polymers, such as polyesters, polysaccharides, polyanhydrides, polycaprolactone, and various combinations thereof. In some cases, the anchor 10 may include a combination of the previously mentioned materials to impart a variable strength and/or degradation time profile in the anchor 10. One example anchor 10 that is configured to rapidly absorb and/or degrade is disclosed in Application Ser. No. 61/031,456, filed Feb. 26, 2008, which is hereby incorporated by reference. However, it is contemplated that any suitable anchor 10 may be used, as desired.

Filament 14 may include a proximal end, a distal end, with a length extending therebetween. The distal end of the filament 14 may be coupled to the anchor 10 with the filament 14 extending proximally therefrom and through the tissue tract 34. In some cases, the anchor 10 may include a raised portion including an eyelet to facilitate attachment of the distal end of the filament 14 to the anchor. In other cases, the distal end of the filament 14 may be molded into the anchor 10, passed through an opening in the anchor 10, or otherwise attached, connected, or secured to the anchor 10, as desired.

The filament 14 may include a biodegradable material so that, over time, the filament 14 is degraded, eroded, and/or absorbed in the body. In some cases, the filament 14 may include a PLGA, PLLA, PGA or other degradable or erodable polymers, such as polyesters, polysaccharides, polyanhydrides, polycaprolactone, and various combinations thereof. In some cases, the filament 14 can include a suture material, which may be a biodegradable suture.

In the illustrative embodiment, the plug 12 can be disposed about at least a portion of the filament 14 adjacent to the anchor 10 in the tissue tract 34 and/or opening of the vessel wall 32. The plug 12 may be configured to fill the space in the tissue tract 22 adjacent to the vessel 30 and/or the opening in the vessel wall 32 to close and/or seal the vessel 30 opening and/or tissue tract 34. In some example, the plug 12 may include a material that swells to fill space in the tissue tract 34 and/or vessel wall 32 opening, such as by elastic expansion, fluid absorption, chemical reaction, as well as any other suitable swelling and/or expansion. The plug 12 can be configured to promote hemostasis and/or clotting adjacent to the vessel 30. In one example, the plug may include a collagen, gelatin foam, PEG, starch powder, any suitable hemostatic material, any suitable clot-promoting material, as well as any other suitable material, as desired. In some cases, other materials can be used to provide control of thrombogenicity or hydration. The plug 12 may include a biodegradable material so that, over time, the plug 12 is degraded, eroded, and/or absorbed in the body.

In the illustrative embodiment, the plug 12 may be generally cylindrical in shape with a lumen extending therethrough. As illustrated, the plug 12 is shown in an axially compressed state after it has been deployed in the tissue tract 20.

Some examples of plugs and plug materials that may be used in the closure device are disclosed in application Ser. No. 12/390,289, filed on the even date herewith, which is hereby incorporated by reference. In some cases, the plug 12 can include one or more voids, notches, slits, or other modifications to provide a desired axial compression of plug 12. Examples of plugs that may include voids, notches, slits, or other modification are disclosed in application Ser. No. 12/389,960, filed on the even date herewith, which is hereby incorporated by reference. In some cases, the illustrative plug 12 can be processed to have desired expansion characteristics. For example, the plug 12 can be tenderized to break down cell walls to increase the rate of expansion of the plug 12. Examples of plugs that have been tenderized or otherwise processed and methods of tenderizing or otherwise processing are disclosed in application Ser. No. 12/390,067, filed on the even date herewith, which is hereby incorporated by reference.

In the illustrative embodiment, the locking element 16 can be a knot. The knot 16 can be used to help secure the plug 12 relative to the anchor 10. In one example, a knot 16 can be disposed about at least a portion of the filament 14 proximal of the anchor 10. The knot 16 can be configured to slide over the filament 14 and compress the plug 12. In some cases, the knot 16 can be slide distal over the filament 14 to compress the plug 12. In some cases, the knot 16 may be a compression knot exerting a radial force on the filament 14. As such, the knot 16 may be configured to have a corresponding friction force of 0.5 pounds, 1.0 pound, 1.5 pounds, 2.0 pounds, 2.5 pounds, 3.0 pounds, or any other friction force, as desired. For example, the knot 16 may have a friction force of at least 0.5 pounds. In another example, the knot 16 may have a friction force of at least one pound, two pounds, three pounds, or any other friction force, as desired. In any event, the knot 16 may be configured to have a friction force greater than the rebound force of the plug 12 to prevent the plug 12 expanding after compression. The rebound force of the plug 12 may be the force of the plug 12 trying to expand in the axial direction after compression.

In the illustrative embodiment, the knot 16 may be independent of the filament 14. The knot 16 may include a suture that is independent of the filament 14. In some cases, the knot 16 may be include a suture that has a larger radial diameter than the filament 14 so that the knot 16 has a sufficient size to contact the proximal end of the plug 12 for axial compression and not penetrating into the plug 12.

In the illustrative embodiment, the knot 16 may include a degradable material so that over time, it is degraded or eroded and no longer present in the body. In some cases, the locking element 16 may include a PLGA, PLLA, PGA or other degradable or erodable polymers, such as polyesters, polysaccharides, polyanhydrides, polycaprolactone, and various combinations thereof.

FIGS. 2 and 3 are schematic diagrams of the illustrative knot 16 of FIG. 1 disposed about the filament 14. As shown in FIG. 2, the knot 16 can be formed by loosely wrapping a suture 17 around the filament 14 a number of times to define a lumen therethrough. As illustrated in FIG. 2, the suture 17 can be wrapped around the filament 14 five times. However, it is contemplated that the suture 17 may be wrapped around the filament 14 one time, two times, three times, four times, five times, six times, seven times, eight times, nine times, ten times, or any number of times, as desired. Then, both ends of the suture 17 may be passed through the lumen defined by the turns of the knot 16.

Suture 17 ends can then by pulled to tighten the knot 16 as shown in FIG. 3. In other words, a tensioning force can be applied to the ends of the suture 17 to tighten the knot 16. The tensioning force to tighten the knot 16 may correspond to the compressive force that the knot 16 exerts on the filament. For example, the greater the tensioning force, the greater the compressive force exerted by the knot 16 on the filament 14. With the knot 16 tightly tied, the ends of the suture 17 can be removed from the knot 16.

In the illustrative embodiment, the suture 17 of knot 16 may be separate and distinct from the filament 17. In other words, the knot 16 may be independent of the filament 14. Further, in some cases, the knot 16 may be constructed of a suture 17 that is has a different radial diameter than the suture used for the filament 14. In one illustrative example, the filament 14 may have a diameter of about 0.014 to 0.016 millimeters and the suture 17 of the knot 16 may have a diameter of about 0.016 to 0.018 millimeters. However, it is contemplated that any combination of suture sizes may be used, as desired. In this illustrative example and when five turns are used, the length of the knot 16 may be about 0.0890 to 0.091 millimeters. In addition, in this example, the diameter of the loose knot 16 may be about 0.069 millimeters and the diameter of the tight knot 16 may be about 0.0511 to 0.0532 millimeters. However, any suitable length or width may be used, as desired.

Figure 4:
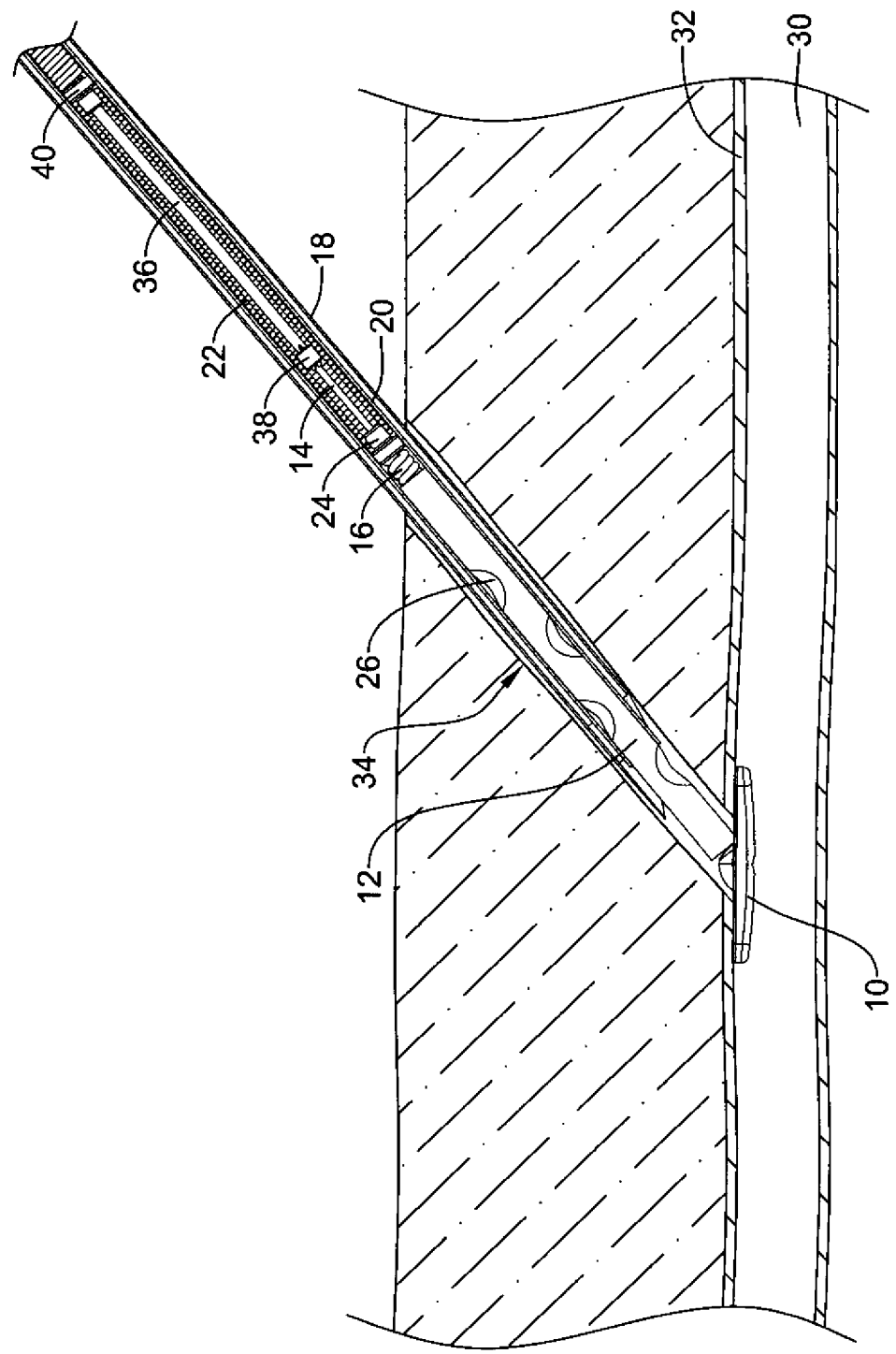
FIGS. 4 and 5 are schematic diagrams of an illustrative embodiment of a device for sliding the knot along the filament to deploy the plug within the opening of the vessel wall and/or tissue tract.
Figure 5:
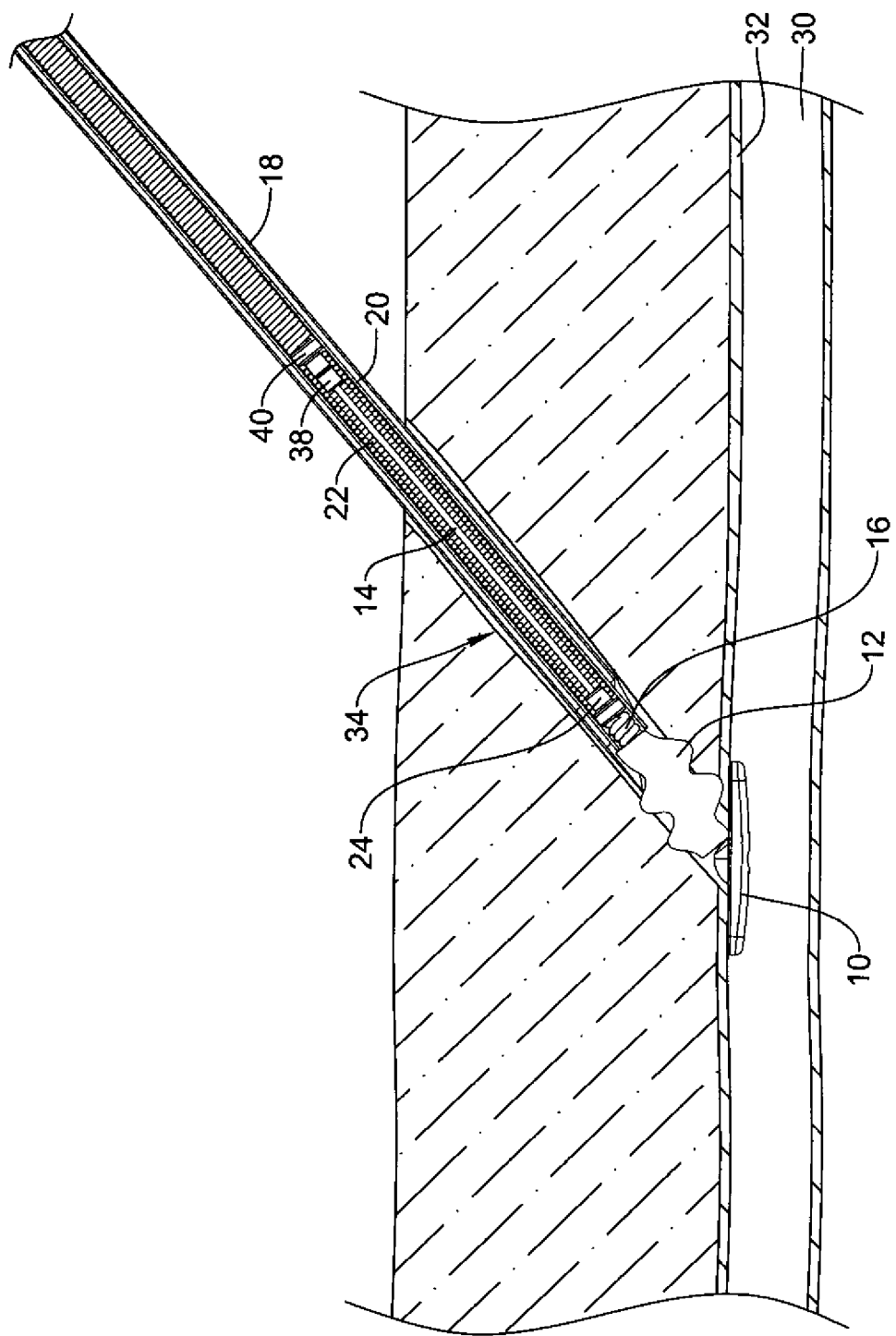

FIGS. 4 and 5 are schematic diagrams of an illustrative embodiment of a device for sliding the knot 16 along the filament 14 to deploy the plug 12 within the opening of the vessel wall 32 and/or tissue tract 34. In the illustrated embodiment, an insertion sheath 18 may be disposed at least partially in the tissue tract 34 for providing access to the opening in the vessel wall 32. The device for delivery the anchor 10, plug 12, filament 14, and knot 16 can include a device sheath 20 configured to pass into the insertion sheath 18. As shown, the device may include a push rod 22 having a distal end coupled to a plunger compression bead 24. The plunger compression bead 24 may be disposed adjacent to the knot 16. In the illustrative example, the push rod 22 can include one or more coils configured to slide over the filament 14.

In the illustrative example, the device may include an automatic filament release mechanism. This mechanism may include a collet 36 coupled to the filament 14 and a collet locking ring 38 configured to releasably engage the filament 14. As the push rod 22 is advanced distally, a filament release bead 40 disposed in the push rod 22 and about the collet 36, may be advanced distally over the collet 36 and engage the collet locking ring 38. As the push rod 22 continues to advance distally, the filament release bead 40 may disengage the collet locking ring 38 from the collet 36 releasing the filament 14 from the device. An example of an implantation device that may be used with the illustrative anchor 10, plug 12, filament 14, and knot 16 is disclosed in application Ser. No. 12/390,241, filed on the even date herewith, which is hereby incorporated by reference.

As illustrated in FIG. 4, the anchor 10 is seated against the interior of the vessel wall 32 or arteriotomy. The filament 14 is coupled to the anchor 10 and extends proximally through the tissue tract 34. The plug 12 is disposed over the filament 14 adjacent the anchor 10 and the knot 16 is disposed about the filament 14 proximal of the plug 12. The plug 12, filament 14, and knot 16 may be disposed, at least partially, within the device sheath 20. As illustrated, both the insertion sheath 18 and the device sheath 20 may be retracted a distance from the anchor 10 and/or opening in the vessel wall 32 to provide an area for plug 12 deployment. In the illustrative example, the distance may be about one-quarter the length of the plug 12. However, it is contemplated that any suitable distance may be used, as desired.

FIG. 5 shows the plug 12 in a compressed state after the device has been actuated advancing the push rod 22 to slide the knot 16 distally over the filament 14 and compress the plug 12. As discussed previously, the knot 16 may have a friction force on the filament 14, which may be greater than the rebound force of the plug 12. The force exerted by the push rod 22 and plunger compression bean 24 on the knot 16 may be greater than the friction force of the knot 16. As such, the knot 16 can maintain the plug 12 in a compressed state when the device, including the push rod 22, plunger compression bead 24, device sheath 20, and insertion sheath are removed. With the device and insertion sheath 18 removed, the anchor 10, plug 12, filament 14, and knot 16 may remain in the tissue tract 34 and/or vessel wall 32 opening, as shown in FIG. 1.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A device for sealing an opening in a vessel wall and/or tissue tract, the device comprising:
    an anchor member configured to be disposed adjacent to an interior surface of the vessel wall adjacent the opening in the vessel wall;
    a filament member having a distal end coupled to the anchor member and configured to extend proximally through the vessel opening and/or tissue tract;
    a plug member disposed about at least a portion of the filament member and in direct contact with the anchor member; and
    a knot member disposed and tightened about the filament member proximal of the plug member, wherein the tightened knot member is configured to move over the filament member and axially compress the plug member against the anchor member, wherein the knot member is independent of the filament member;
    wherein the knot member includes a first suture having a diameter larger than a diameter of the filament member.

2. The device of claim 1, wherein the filament member includes a second suture.

3. The device of claim 1 wherein the knot member exerts a compressive force on the filament member.

4. The device of claim 3 wherein the compressive force of the knot member on the filament member correlates to a friction force that is greater than a rebound force of the plug member, wherein the rebound force of the plug is a force of the plug trying to expand in the axial direction after compression.

5. The device of claim 3 wherein the knot member has a friction force of at least 0.5 pounds.

6. The device of claim 3 wherein the knot member has a friction force of at least two pounds.

7. A device for sealing an opening in a vessel wall and/or tissue tract, the device comprising:
    a biodegradable anchor member configured to be disposed adjacent to an interior surface of the vessel wall adjacent the opening in the vessel wall;
    a first suture member having a distal end coupled to the anchor member and configured to extend proximally through the vessel opening and/or tissue tract;
    a plug member disposed about at least a portion of the first suture member adjacent to and in direct contact with the anchor member; and
    a second suture member includes a first end, a second end, and an intermediate portion having a number of turns defining a lumen, wherein the first end and second end are passed through the lumen, wherein the second suture member is disposed and tightened about the first suture member proximal of the plug member, wherein the second suture member exerts a compressive force on the first suture member, wherein the second suture member is independent of the first suture member;

wherein the second suture member has a diameter that is larger than the first suture member;

wherein the second suture member is configured to move over the first suture member and axially compress the plug member against the anchor member.

8. The device of claim 7 wherein the compressive force of the second suture member on the first suture member is related to a friction force of the second suture, wherein the friction force of the second suture is greater than a rebound force of the plug member, wherein the rebound force of the plug is a force of the plug trying to expand in the axial direction after compression.

9. The device of claim 8 wherein the second suture member has a friction force of at least two pounds.

10. The device of claim 8 further comprising a push rod configured to exert a force on the second suture member greater than the friction force of the second suture member on the first suture member.

\* \* \* \* \*